United States Patent
Goldsteen et al.

[19]

[11] Patent Number: 6,136,007
[45] Date of Patent: *Oct. 24, 2000

[54] APPARATUS FOR HANDLING TUBING USED IN MEDICAL PROCEDURES

[75] Inventors: David S. Goldsteen, Minneapolis; Thomas J. Bachinski, Lakeville; Daniel J. Sullivan, Medina, all of Minn.

[73] Assignee: St. Jude Medical Cardiovascular Group, Inc,, Minneapolis, Minn.

[*] Notice: This patent is subject to a terminal disclaimer.

[21] Appl. No.: 09/303,224

[22] Filed: Apr. 30, 1999

Related U.S. Application Data

[63] Continuation of application No. 08/839,298, Apr. 17, 1997, Pat. No. 5,931,842.

[51] Int. Cl.[7] .................................................. A61F 11/00
[52] U.S. Cl. ............................ 606/108; 623/1; 623/12
[58] Field of Search .......................... 606/108, 191–200; 623/1, 11, 12; 604/96–104, 96.01, 101.01, 101.02, 101.04

[56] References Cited

U.S. PATENT DOCUMENTS

| | | |
|---|---|---|
| 4,577,631 | 3/1986 | Kreamer . |
| 4,592,754 | 6/1986 | Gupte et al. . |
| 4,911,163 | 3/1990 | Fina . |
| 5,331,975 | 7/1994 | Bonutti . |
| 5,415,636 | 5/1995 | Forman . |
| 5,462,592 | 10/1995 | Simpson et al. . |
| 5,464,449 | 11/1995 | Ryan et al. . |
| 5,476,505 | 12/1995 | Limon . |
| 5,569,296 | 10/1996 | Marin et al. . |
| 5,571,086 | 11/1996 | Kaplan et al. . |
| 5,676,670 | 10/1997 | Kim . |
| 5,730,698 | 3/1998 | Fischell et al. . |
| 5,931,842 | 8/1999 | Goldsteen et al. ................ 606/108 |

FOREIGN PATENT DOCUMENTS

| | | |
|---|---|---|
| 0 508 473 A2 | 10/1992 | European Pat. Off. . |
| 0 649 637 A1 | 4/1995 | European Pat. Off. . |
| 0 723 786 A1 | 7/1996 | European Pat. Off. . |
| WO 86/06285 | 11/1986 | WIPO . |
| WO 90/15582 A1 | 12/1990 | WIPO . |

*Primary Examiner*—Glenn K. Dawson
*Attorney, Agent, or Firm*—Fish & Neave; Robert R. Jackson; G. Victor Treyz

[57] ABSTRACT

Methods and apparatus are provided for such uses as attaching grafts of tubing (e.g., lengths of saphenous vein) between sites in a patient's body via the patient's existing arteries and veins. Grafts may be held in place during graft delivery using a partially inflated proximal balloon and a partially inflated distal balloon which frictionally engage axially spaced portions of the graft (e.g., pronged attachment rings that pierce the graft adjacent its ends). After aligning the distal balloon and distal end of the graft with the distal attachment site, the distal balloon may be further inflated to help attach the distal end of the graft to the distal attachment site (e.g., by driving the prongs of the distal attachment ring into the distal attachment site). The proximal balloon may then be inflated to similarly help attach the proximal end of the graft to the proximal attachment site. The balloons are deflated to facilitate withdrawal of the apparatus from the installed graft. The insertion instrument allows the distance between the distal and proximal balloons to be adjusted, thereby accommodating grafts of various lengths. The separation between distal and proximal balloons may be fixed or substantially fixed using a locking mechanism.

72 Claims, 6 Drawing Sheets

APPARATUS FOR HANDLING TUBING USED IN MEDICAL PROCEDURES

This is a continuation, of application Ser. No. 08/839,298, filed Apr. 17, 1997, now U.S. Pat. No. 5,931,842.

BACKGROUND OF THE INVENTION

This invention relates to handling tubing used in medical procedures. For example, the invention may be used in connection with delivering and installing tubular grafts into a patient's body to repair, replace, or supplement a patient's natural body organ structures or tissues. The invention is especially useful in connection with inserting such grafts into a patient through the patient's existing arteries and veins.

Several procedures are known for revascularizing the human heart in order to treat a patient with one or more occluded coronary arteries. The earliest of these procedures to be developed involves exposing the heart by means of a midline sternotomy. Following surgical exposure of the heart, the patient's aorta and vena cava are connected to a heart/lung machine to sustain vital functions during the procedure. The beating of the heart is stopped to facilitate performance of the procedure. Typically, a suitable blood vessel such as a length of the patient's saphenous (leg) vein is harvested for use as a graft. The graft is used to create a new, uninterrupted channel between a blood source, such as the aorta, and the occluded coronary artery or arteries downstream from the arterial occlusion or occlusions.

A variation of the above procedure involves relocating a mammary artery of the patient to a coronary artery.

Although the above-described sternotomy procedures are increasingly successful, the high degree of invasiveness of these procedures and the requirement of these procedures for general anesthesia are significant disadvantages. Indeed, these disadvantages preclude use of sternotomy procedures on many patients.

More recently, less invasive procedures have been developed for revascularizing the heart. An example of these procedures is known as thoracostomy, which involves surgical creation of ports in the patient's chest to obtain access to the thoracic cavity. Specially designed instruments are inserted through the ports to allow the surgeon to revascularize the heart without the trauma of a midline sternotomy. Drugs may be administered to the patient to slow the heart during the procedure. Some thoracostomy procedures involve relocating a mammary artery to a coronary artery to provide a bypass around an occlusion in the coronary artery.

Thoracostomy bypass procedures are less traumatic than sternotomy bypass procedures, but they are still too traumatic for some patients. Also, the number of required bypasses may exceed the number of mammary arteries, thereby rendering thoracostomy procedures inadequate to fully treat many patients.

Another technique for revascularizing the human heart involves gaining access to the thoracic cavity by making incisions between the patient's ribs. This procedure is known as thoracotomy. It is also substantially less traumatic than midline sternotomy, but it is still too traumatic for some patients.

In view of the foregoing, even less traumatic approaches have been developed for revascularizing a patient, as described in Goldsteen et al. U.S. patent application Ser. No. 08/745,618, filed Nov. 7, 1996, and hereby incorporated by reference herein in its entirety. With such approaches, grafts (e.g., of saphenous veins) can be delivered to an operative site in the patient through the patient's existing arteries and veins. Grafts are typically inserted between two attachment sites in the patient's existing body organs (e.g., between a site along the patient's aorta and a site along the coronary artery downstream from a coronary artery occlusion).

A number of instruments are used to perform the different tasks associated with such a grafting procedure. One important instrument is the tubular graft insertion instrument used for graft delivery and attachment. Prior to insertion of the graft in the body, the graft is placed over the end of this instrument. Two small inflatable balloons, which are located a fixed distance from one another along the length of the instrument, are partially inflated to hold the graft in place. The graft is then inserted into the patient and aligned with the attachment site. When each end of the graft is aligned, the corresponding balloon is further inflated to drive prongs of a corresponding pronged attachment ring through the graft into the patient's tissue at the attachment site.

This type of graft insertion instrument can be used in a variety of situations. However, the fixed spacing between the two small balloons restricts the lengths of grafts that may be inserted with any given instrument. It is therefore an object of the present invention to provide methods and apparatus for inserting variable length grafts into a patient.

SUMMARY OF THE INVENTION

This and other objects of the invention are accomplished in accordance with the principles of the present invention by providing methods and apparatus in which grafts of various lengths are accommodated by a graft insertion instrument having balloons with a variable axial separation. The distance between the balloons can be adjusted to match the length of a given graft. The variable axial separation between balloons may then be substantially fixed using a securing or locking mechanism.

A preferred embodiment of the graft insertion instrument uses coaxial inner and outer tubes. The inner and outer tubes have associated inflatable annular or circumferential balloons. The balloons are partially inflated to frictionally engage respective axially spaced portions of the interior of the graft (e.g., pronged attachment rings at respective opposite ends of the graft). Prior to graft delivery, the graft may be held by the prongs of the attachment rings while the inner tube is moved within the outer tube to adjust the spacing of the balloons and attachment rings to match the length of the graft. During graft delivery, the spacing between the balloons is substantially fixed by the above-mentioned securing or locking mechanism, which substantially prevents slippage between the inner and outer tubes. Once the graft has been delivered to the attachment site, the balloons may be more fully inflated to drive the prongs on the attachment rings through the ends of the graft into the patient's tissue.

The foregoing is only illustrative of certain aspects of the invention, and further features of the invention, its nature and various advantages will be more apparent from the accompanying drawings and the following detailed description of the preferred embodiments.

DETAILED DESCRIPTION OF THE PREFERRED EMBODIMENTS

Figure 1:
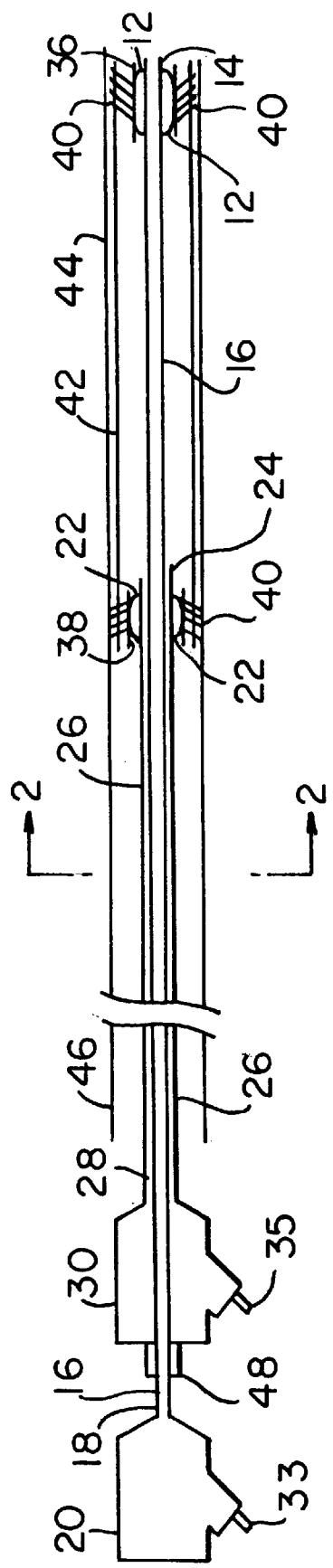
FIG. 1 is a simplified longitudinal sectional view showing a portion of illustrative tube handling apparatus in accordance with this invention.

An illustrative tube handling instrument 10 in accordance with the present invention is shown in FIG. 1. One possible use of instrument 10 is in connection with instrumentally delivering and installing graft tubing in a patient in need of such treatment. This type of use of instrument 10 will be discussed in detail in the immediately following portions of this specification, but it will be appreciated that the invention has many other possible uses, examples of which will be mentioned later in the specification.

In the illustrative instrument 10, balloon 12 is mounted to and extends circumferentially around the distal end 14 of inner tube 16. The proximal end 18 of inner tube 16 is attached to handle 20. Balloon 22 is mounted to and extends circumferentially around the distal end 24 of outer tube 26. The proximal end 28 of outer tube 26 is attached to handle 30.

Figure 2:
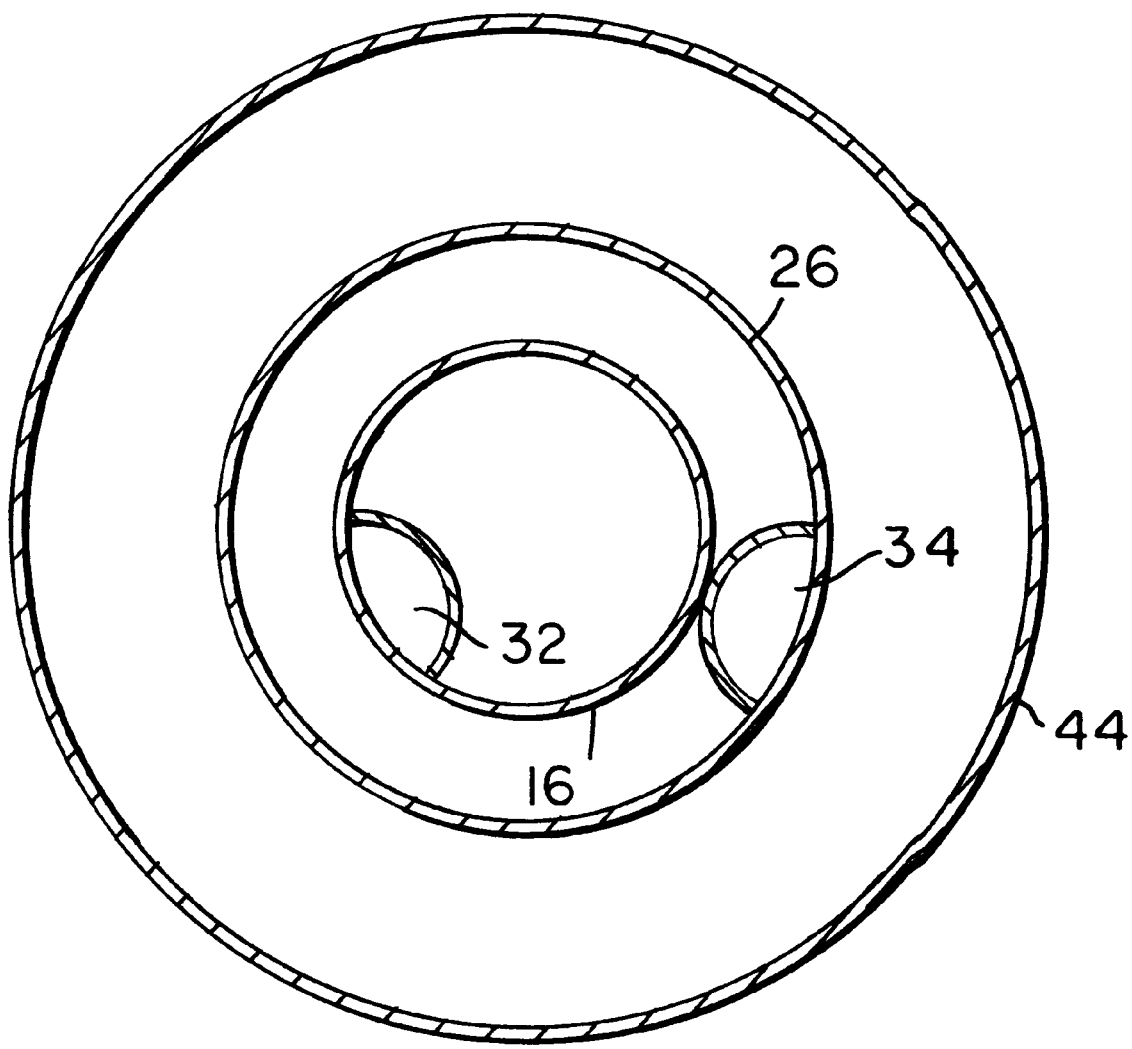
FIG. 2 is a cross-sectional view of the apparatus of FIG. 1 taken along the line 2—2 that shows the use of separate lumens for the inner and outer tubes.

As shown in FIG. 2, inner tube 16 has an associated lumen 32, which communicates with balloon 12. Balloon 12 may be inflated or deflated by controlling the introduction of pressurized gas or liquid (herein collectively called "fluid") through lumen 32. Outer tube 26 has an associated lumen 34, which communicates with balloon 22. Balloon 22 may be inflated or deflated by controlling the introduction of pressurized fluid through lumen 34. Pressurized fluid is introduced into lumen 32 via port 33 (FIG. 1). Port 35 (FIG. 1) in handle 30 is used to introduce fluid into lumen 34.

As shown in FIG. 1, balloons 12 and 22 may be partially inflated to hold the ends of graft tubing 42. For example, the partially inflated balloons frictionally engage respective attachment rings 36 and 38 on graft 42. Attachment rings 36 and 38 have prongs 40, which may pierce graft 42.

The graft assembly shown in FIG. 1 is preferably surrounded by delivery tube 44 prior to insertion in the patient's body. During insertion, the proximal portion of delivery tube 44 that contains graft 42 is inserted into a vein or artery of the patient via a standard catheter (not shown). Alternatively, tube 44 may itself be or perform the function of the catheter mentioned in the previous sentence. The physician can control the placement of delivery tube 44 by physically manipulating the proximal end 46 of delivery tube 44, which remains outside the patient's body. The physician can control placement of graft 42 by manipulating handles 20 and 30.

Graft 42 may be a length of natural tubing such as a harvested saphenous vein, artificial tubing, or a combination of such materials. Prior to insertion in the patient, graft 42 is typically cut to its desired final length by the physician. The axial separation between balloons 12 and 22 may be adjusted to accommodate the length of the graft by reciprocating inner tube 14 within outer tube 26 using handles 20 and 30. When the desired axial separation between balloons 12 and 22 has been achieved, locking mechanism 48 is engaged, thereby preventing or at least resisting further movement between balloons 12 and 22.

Figure 3:
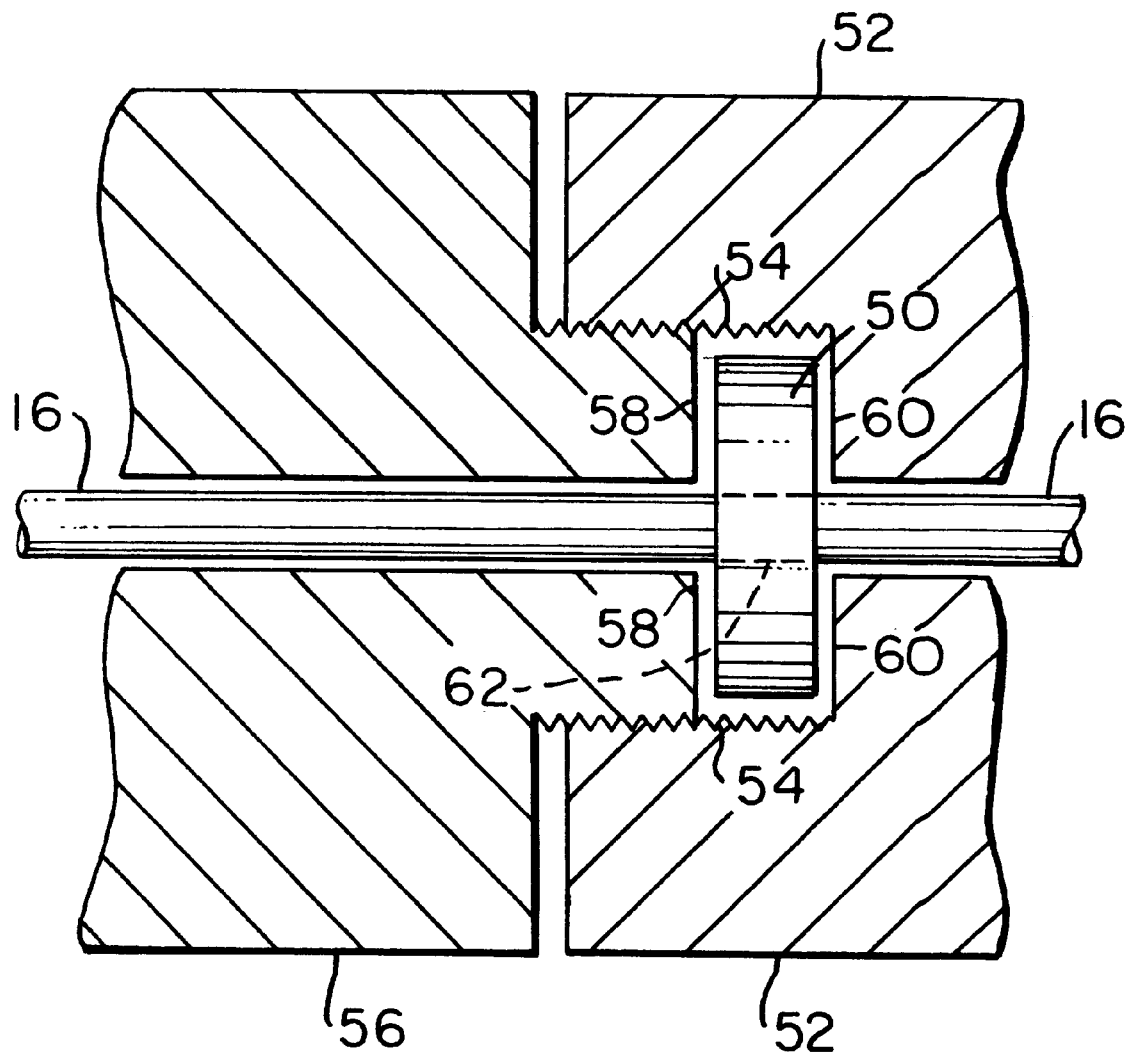
FIG. 3 is a side sectional view of an illustrative locking mechanism in accordance with the invention.

An illustrative locking mechanism 48 is shown in more detail in FIG. 3. In the unlocked configuration shown in FIG. 3, inner tube 16 reciprocates freely (left or right as viewed in FIG. 3) through an aperture in resilient ring 50. Member 52 is mounted to handle 30 (not shown in FIG. 3) and has a threaded bore 54 for receiving threaded member 56. When it is desired to lock outer tube 26 to inner tube 16, member 56 is screwed into member 52, thereby axially compressing ring 50 between opposing end faces 58 and 60. The axial compression of ring 50 causes the inner diameter 62 of ring 50 to contract and frictionally engage inner tube 16. Because member 52 is attached to handle 30, which is attached to outer tube 26, engaging tube 16 with ring 50 prevents tube 16 from moving relative to tube 26.

The particular locking mechanism 48 shown in FIG. 3 is only illustrative, and any other suitable locking or securing structure may be used. One example of another locking mechanism is a set screw provided through handle 30 to selectively bear on inner tube 16 where it passes through handle 30. Another example of a locking mechanism is a clamp surrounding inner tube 16 and connected to outer tube 26. Tightening the clamp causes it to engage inner tube 16 and thereby lock tubes 16 and 26 together.

One of the advantages of instrument 10 is that it allows the physician to adjust the spacing between balloons 12 and 22 to accommodate grafts 42 of various lengths. In addition, using locking mechanism 48 to lock tubes 16 and 26 prevents relative movement between balloons 12 and 22. Preventing relative movement between balloons 12 and 22 ensures that graft 42 is not damaged by relative movement between balloons 12 and 22 during graft insertion and ensures that the distance between the ends of the graft (e.g., between attachment rings 36 and 38) is properly maintained. Locking the balloon spacing also ensures that the ends of graft 42 are separated by the proper amount for graft attachment.

Figure 4:
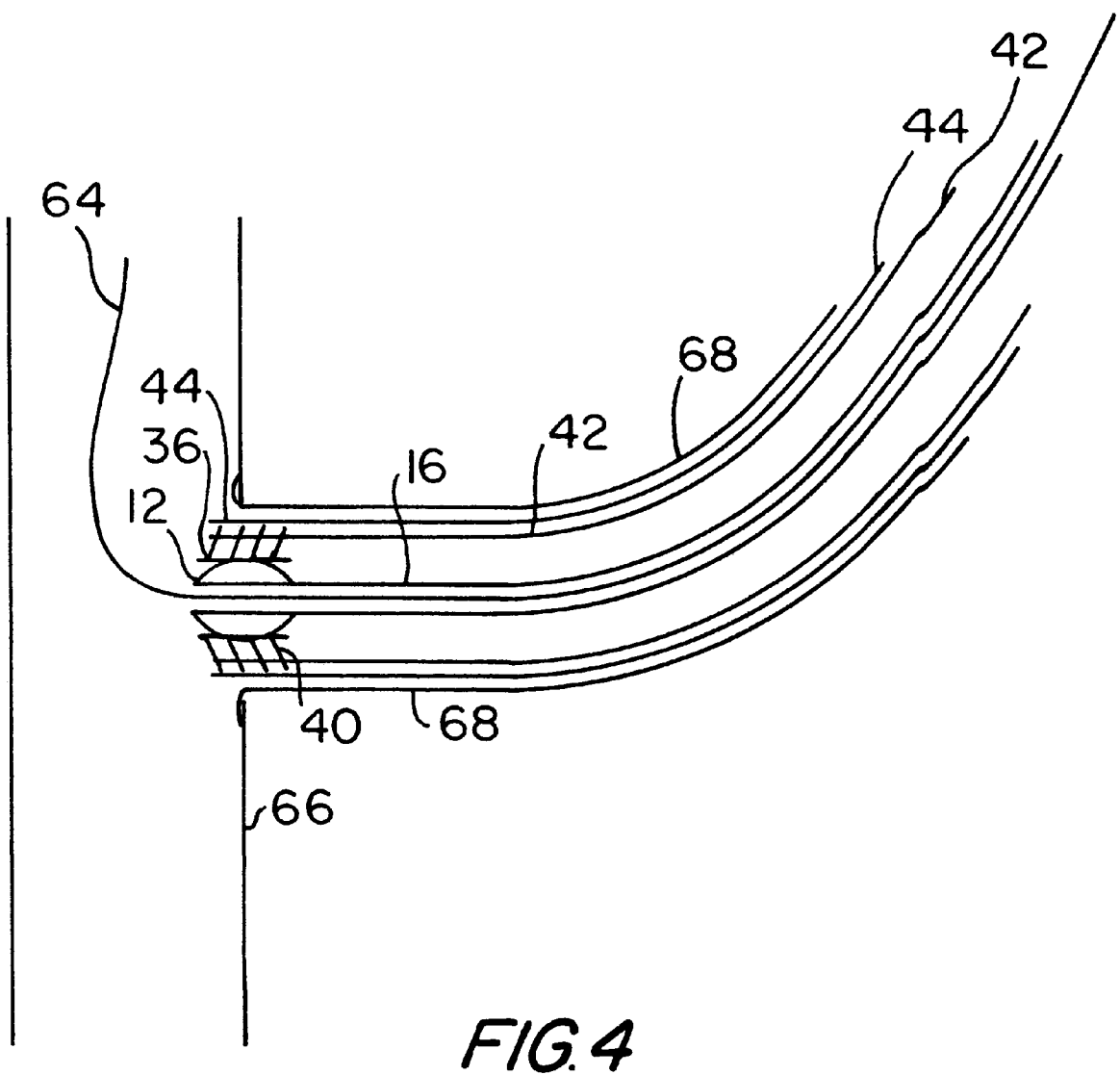
FIGS. 4–6 are diagrams illustrating the insertion of a natural graft to line a previously installed artificial graft.
Figure 5:
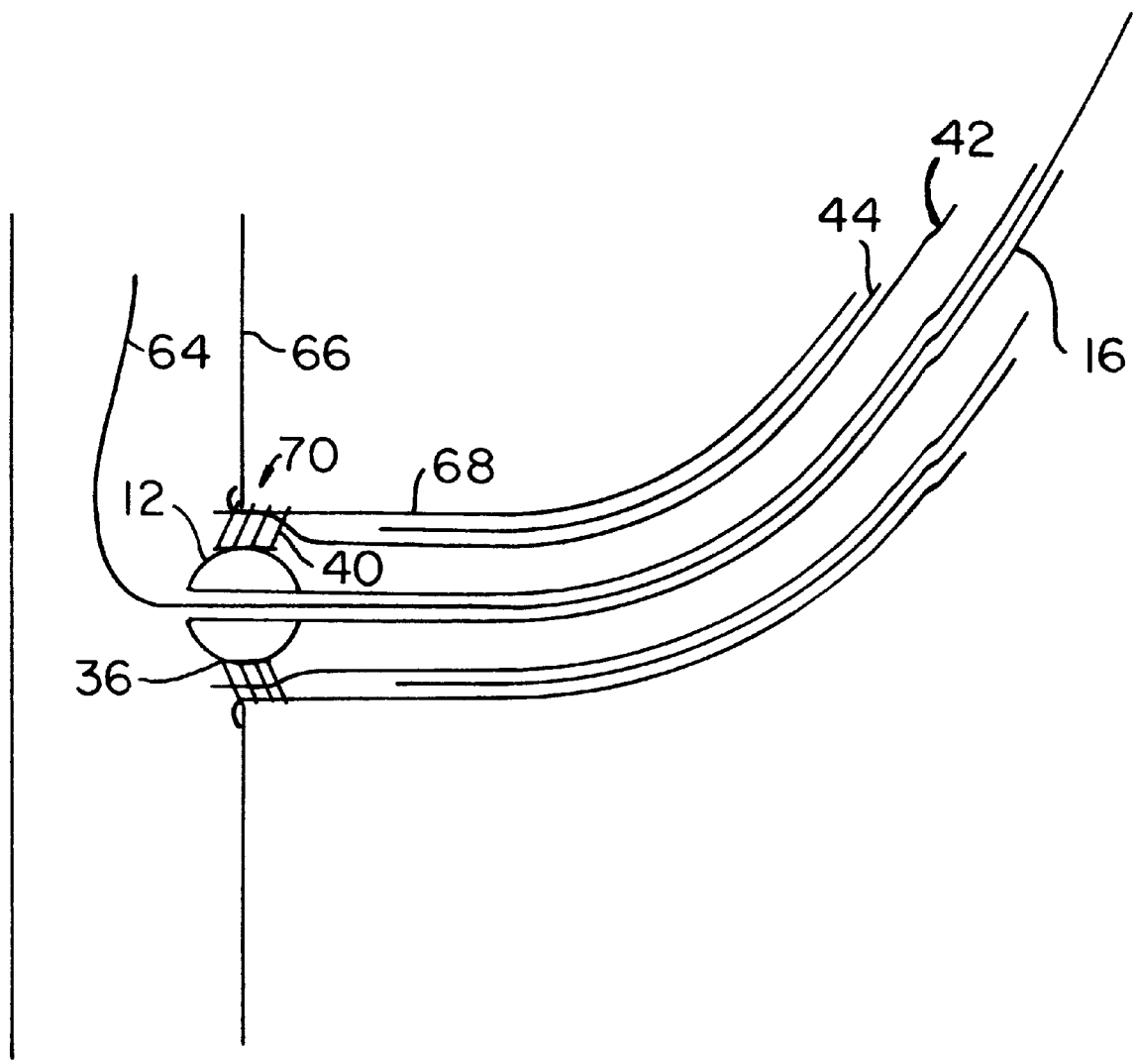
Figure 6:
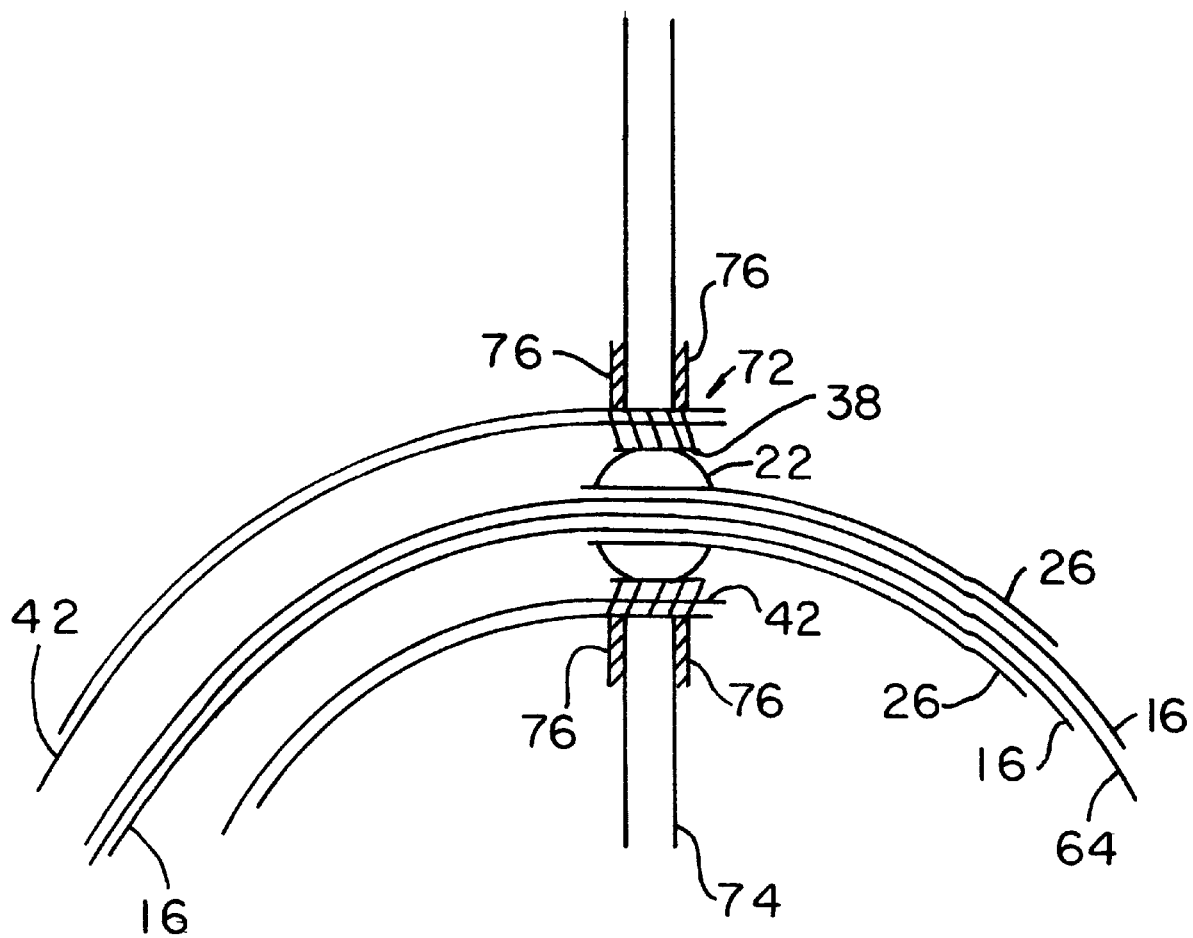

Part of an illustrative graft insertion procedure using instrument 10 is shown in FIGS. 4–6. The procedure shown in FIGS. 4–6 is a lining procedure in which a graft of natural tubing 42 (e.g., a length of harvested saphenous vein) is used to line a previously installed artificial tube 68 (e.g., to improve its bio-compatibility). However, it will be appreciated that similar graft insertion steps may be used to install various other types of tubing in a patient. For example, instrument 10 may be used for installing artificial tubing (either by itself or as a prelude to installing a lining of natural tubing), installing natural tubing by itself, simultaneously installing natural and artificial tubing (e.g., natural tubing concentrically inside artificial tubing), etc.

As shown in FIG. 4, a wire 64 may be used to guide the distal end of delivery tube 44 (e.g., into artery 66 via previously installed artificial graft 68). Wire 64 and graft 68 may have been previously installed using techniques described in the abovementioned Goldsteen et al. reference. Delivery tube 44 and graft 42 (which is held by partially inflated balloons 14 and 22) are advanced along wire 64 through artificial graft 68 until prongs 40 of attachment ring 36 are adjacent to the intended distal site for graft attachment.

Once the distal end of graft 42 and attachment ring 36 have been properly aligned with the distal attachment site as shown in FIG. 4, delivery tube 42 is retracted in the proximal direction and balloon 14 is further inflated, as shown in FIG. 5. This step sets prongs 40 of ring 36 through graft 42 and artificial graft 68 into the tissue of artery 66 at attachment site 70.

After attaching the distal end of graft 42, delivery tube 44 is withdrawn in the proximal direction to expose proximal attachment ring 38, which is aligned with attachment site 72 for the proximal end of graft 42, as shown in FIG. 6. The proximal end of graft 42 is attached with ring 38 by further inflating balloon 22. The illustrative attachment site 72 shown in FIG. 6 is in portal wall 74 and has previously installed axially spaced resilient flaps 76. The procedure is completed by deflating balloons 12 and 22 and withdrawing tubes 16, 26, and 44, and wire 64 from the patient's body.

To allow radiologic observation of instrument 10 during graft insertion, tubes 16, 26, and 44 may have radiologic (e.g., radio-opaque or fluoroscopically viewable) markers at suitable locations to help the physician place the structure where desired in the patient's body.

It will be understood that the foregoing is only illustrative of the principles of the invention, and that various modifications can be made by those skilled in the art without departing from the scope and spirit of the invention. For example, the use of balloons 12 and 22 as radially enlargeable structures is only illustrative, and other types of radially enlargeable structures (e.g., mechanically enlargeable structures) may be used if desired. The use of attachment rings like 36 and 38 is optional and such structures can be omitted if the procedure being performed does not require them. If structures like 36 and 38 are needed they can have any suitable construction, the particular construction shown and described herein being only one example.

The invention claimed is:

1. A system for delivering grafts of various lengths to attachment sites in patients' bodies through the patients' existing body organ tubing, the system comprising:
   a graft;
   first and second substantially longitudinal and axially aligned support structures;
   a distal structure mounted on the first support structure engaging a distal portion of the graft;
   a proximal structure mounted on the second support structure engaging a proximal portion of the graft, wherein:
      the first and second support structures are axially reciprocable relative to one another to adjust the spacing between the distal and proximal structures; and
      the first and second support structures are configured to deliver the graft to an attachment site within a patient and install the graft at the attachment site so that the graft is at least partly outside the patient's existing body organ tubing.

2. The system defined in claim 1 further comprising:
   a delivery tube surrounding the first and second support structures and the graft during at least part of the graft delivery.

3. The system defined in claim 2 wherein the distal structure is disposed inside the graft during at least part of the graft delivery.

4. The system defined in claim 3 wherein the distal structure is selectively radially enlargeable to selectively engage the graft.

5. The system defined in claim 4 further comprising:
   a control structure that extends distally from a proximal portion of the first support structure to the distal structure and that is configured to allow radial enlargement of the distal structure to be remotely controlled from adjacent the proximal portion.

6. The system defined in claim 5 wherein:
   the distal structure includes an inflatable balloon; and
   the control structure includes an inflation lumen extending along the first structure from the proximal portion to the balloon.

7. The system defined in claim 6 wherein the balloon extends annularly around the first support structure.

8. The system defined in claim 2 wherein the proximal structure is disposed inside the graft during at least part of the graft delivery.

9. The system defined in claim 8 wherein the proximal structure is selectively radially enlargeable to selectively engage the graft.

10. The system defined in claim 9 further comprising:
    a control structure that extends distally from a proximal portion of the second support structure to the proximal structure and that is configured to allow radial enlargement of the proximal structure to be remotely controlled from adjacent the proximal portion.

11. The system defined in claim 10 wherein:
    the proximal structure includes an inflatable balloon; and
    the control structure includes an inflation lumen extending along the second structure from the proximal portion to the balloon.

12. The system defined in claim 11 wherein the balloon extends annularly around the second support structure.

13. The system defined in claim 2 further comprising:
    a securing structure connected between the first and second support structures and configured to selectively secure the first and second structures to one another to substantially maintain a spacing between the distal and proximal structures.

14. The system defined in claim 13 wherein the securing structure is selectively releasable.

15. The system defined in claim 2 further comprising a locking mechanism connected between the first and second support structures and having:
    an unlocked configuration in which the first support structure can move axially relative to the second support structure; and
    a locked configuration in which the first and second support structures are held together to resist relative axial movement between the first and second structures.

16. The system defined in claim 15 wherein the locking mechanism comprises:
    a resilient ring having an inner diameter surrounding the first support structure such that the first support structure moves freely within the ring when the ring is uncompressed; and
    an axial compression structure for axially compressing the resilient ring, so that the inner diameter contracts and frictionally engages the first support structure.

17. The system defined in claim 2 wherein the distal structure comprises a distal inflatable balloon.

18. The system defined in claim 17 wherein the distal inflatable balloon extends circumferentially around the first support structure.

19. The system defined in claim 2 wherein the proximal structure comprises a proximal inflatable balloon.

20. The system defined in claim 19 wherein the proximal inflatable balloon extends circumferentially around the second support structure.

21. The system defined in claim 2 wherein a distal portion of the first support structure is received inside the graft during at least part of the graft delivery.

22. The system defined in claim 2 wherein a distal portion of the second support structure is received inside the graft during at least part of the graft delivery.

23. The system defined in claim 2 wherein:
    the first support structure includes an inner tube;

the second support structure includes an outer tube; and
the inner tube is axially reciprocable within the outer tube.

24. The system defined in claim 2 wherein:
a longitudinal structure is used to guide the first and second support structures during at least part of the use of the system; and
the first support structure contains a passage through which the longitudinal structure passes during at least part of the graft delivery.

25. The system defined in claim 2 further comprising:
a first handle connected to the first support structure; and
a second handle connected to the second support structure.

26. The system defined in claim 2 wherein the first support structure contains a lumen for delivering pressurized fluid to the distal structure.

27. The system defined in claim 2 wherein the second support structure contains a lumen for delivering pressurized fluid to the proximal structure.

28. The system defined in claim 1 wherein the distal structure is disposed inside the graft during at least part of the graft delivery.

29. The system defined in claim 28 wherein the distal structure is selectively radially enlargeable to selectively engage the graft.

30. The system defined in claim 29 further comprising:
a control structure that extends distally from a proximal portion of the first support structure to the distal structure and that is configured to allow radial enlargement of the distal structure to be remotely controlled from adjacent the proximal portion.

31. The system defined in claim 30 wherein:
the distal structure includes an inflatable balloon; and
the control structure includes an inflation lumen extending along the first structure from the proximal portion to the balloon.

32. The system defined in claim 31 wherein the balloon extends annularly around the first support structure.

33. The system defined in claim 1 wherein the proximal structure is disposed inside the graft during at least part of the graft delivery.

34. The system defined in claim 33 wherein the proximal structure is selectively radially enlargeable to selectively engage the graft.

35. The system defined in claim 34 further comprising:
a control structure that extends distally from a proximal portion of the second support structure to the proximal structure and that is configured to allow radial enlargement of the proximal structure to be remotely controlled from adjacent the proximal portion.

36. The system defined in claim 35 wherein:
the proximal structure includes an inflatable balloon, and
the control structure includes an inflation lumen extending along the second structure from the proximal portion to the balloon.

37. The system defined in claim 36 wherein the balloon extends annularly around the second support structure.

38. The system defined in claim 1 wherein the distal structure comprises a distal inflatable balloon.

39. The system defined in claim 38 wherein the distal inflatable balloon extends circumferentially around the first support structure.

40. The system defined in claim 1 wherein the proximal structure comprises a proximal inflatable balloon.

41. The system defined in claim 40 wherein the proximal inflatable balloon extends circumferentially around the second support structure.

42. The system defined in claim 1 wherein a distal portion of the first support structure is received inside the graft during at least part of the graft delivery.

43. The system defined in claim 1 wherein a distal portion of the second support structure is received inside the graft during at least part of the graft delivery.

44. The system defined in claim 1 wherein:
the first support structure includes an inner tube;
the second support structure includes an outer tube; and
the inner tube is axially reciprocable within the outer tube.

45. The system defined in claim 1 wherein:
a longitudinal structure is used to guide the first and second support structures during at least part of the graft delivery; and
the first support structure contains a passage through which the longitudinal structure passes during at least part of the use of the system.

46. The system defined in claim 1 further comprising:
a first handle connected to the first support structure; and
a second handle connected to the second support structure.

47. The system defined in claim 1 wherein the first support structure contains a lumen for delivering pressurized fluid to the distal structure.

48. The system defined in claim 1 wherein the second support structure contains a lumen for delivering pressurized fluid to the proximal structure.

49. A system for delivering grafts of various lengths to attachment sites in patients' bodies through the patients' existing body organ tubing, the system comprising:
a graft;
a first longitudinal structure having a first radially enlargeable structure on a distal portion of the first longitudinal structure, the first radially enlargeable structure and the distal portion of the first longitudinal structure being received in the graft, and the first radially enlargeable structure selectively engaging an axial portion of the interior of the graft and when the first radially enlargeable structure is radially enlarged; and
a second longitudinal structure having a second radially enlargeable structure on a distal portion of the second longitudinal structure, the second radially enlargeable structure and the distal portion of the second longitudinal structure being received in the graft, the second radially enlargeable structure selectively engaging an axial portion of the interior of the graft when the second radially enlargeable structure is radially enlarged, and the second longitudinal structure being mounted for longitudinal movement relative to the first longitudinal structure in order to vary the spacing between the first and second radially enlargeable structures so that the first and second radially enlargeable structures can engage respective axial portions of the interior of the graft.

50. The system defined in claim 49 wherein the first longitudinal structure includes a tubular member.

51. The system defined in claim 49 wherein the second longitudinal structure includes a tubular member.

52. The system defined in claim 51 wherein a proximal portion of the first longitudinal structure is disposed in the tubular member.

53. The system defined in claim 49 wherein the first radially enlargeable structure includes an inflatable balloon.

54. The system defined in claim 53 wherein the inflatable balloon extends annularly around the first longitudinal structure.

55. The system defined in claim 49 wherein the second radially enlargeable structure includes an inflatable balloon.

56. The system defined in claim 55 wherein the inflatable balloon extends annularly around the second longitudinal structure.

57. The system defined in claim 49 further comprising:
- a securing structure configured to selectively resist relative longitudinal movement of the first and second longitudinal structures.

58. The system defined in claim 49 further comprising:
- a control structure configured to control the first radially enlargeable structure from a proximal portion of the first longitudinal structure.

59. The system defined in claim 49 further comprising:
- a control structure configured to control the second radially enlargeable structure from a proximal portion of the second longitudinal structure.

60. The system defined in claim 49 wherein the first radially enlargeable structure is additionally configured to selectively radially enlarge an axial portion of the graft and thereby install the graft in the patient.

61. The system defined in claim 49 wherein the second radially enlargeable structure is additionally configured to selectively radially enlarge an axial portion of the graft and thereby install the graft in the patient.

62. The system defined in claim 49 further comprising:
- a tubular member configured to longitudinally receive in its interior during at least part of the graft delivery the distal portions of the first and second longitudinal structures and the first and second radially enlargeable structures.

63. The system defined in claim 62 wherein the tubular member is configured for insertion along the interior of a blood vessel of the patient.

64. The system defined in claim 49 wherein the distal portions of the first and second longitudinal structures and the first and second radially enlargeable structures are configured for insertion along the interior of a blood vessel of the patient.

65. The system defined in claim 49 wherein the distal portions of the first and second longitudinal structures and the first and second radially enlargeable structures are configured for insertion along the interior of a blood vessel of the patient with the graft extending between the first and second radially enlargeable structures.

66. A system for delivering a graft to a distal attachment site within a patient's body through the patient's existing body organ tubing, comprising:
- a graft having a proximal pronged attachment ring;
- first and second substantially longitudinal and axially aligned support structures;
- a distal structure mounted on the first support structure engaging a distal portion of the graft; and
- a proximal inflatable balloon mounted on the second support structure and configured to frictionally engage the proximal pronged attachment ring when partially inflated, wherein:
- the first and second support structures are axially reciprocable relative to one another to adjust the spacing between the distal and proximal structures; and
- the graft is held by the prongs of the proximal pronged attachment ring.

67. The system defined in claim 66 wherein the proximal balloon drives the prongs of the proximal pronged attachment ring through the graft and into the patient's tissue at the distal attachment site when the proximal balloon is further inflated during at least part of graft delivery.

68. A system for delivering a graft to a distal attachment site within a patient's body through the patient's existing body organ tubing, comprising:
- a graft having a distal pronged attachment ring;
- first and second substantially longitudinal and axially aligned support structures;
- a distal inflatable balloon mounted on the first support structure and configured to frictionally engage the proximal pronged attachment ring when partially inflated; and
- a proximal structure mounted on the second support structure engaging a proximal portion of the graft, wherein:
  - the first and second support structures are axially reciprocable relative to one another to adjust the spacing between the distal and proximal structures;
  - the graft is held by the prongs of the distal pronged attachment ring.

69. The system defined in claim 68 wherein the distal balloon drives the prongs of the distal pronged attachment ring through the graft and into the patient's tissue at the distal attachment site when the distal balloon is further inflated during at least part of graft delivery.

70. A system for delivering a graft to a distal attachment site within patient's body through the patient's existing body organ tubing, comprising:
- a graft having distal and proximal pronged attachment rings;
- first and second substantially longitudinal and axially aligned support structures;
- a distal inflatable balloon mounted on the first support structure and configured to frictionally engage the distal pronged attachment ring when partially inflated; and
- a proximal inflatable balloon mounted on the second support structure configured to frictionally engage the proximal pronged attachment ring when partially inflated; wherein
- the first and second support structures are axially reciprocable relative to one another to adjust the spacing between the distal and proximal structures;
- the graft is held by the prongs of the distal and proximal pronged attachment rings.

71. The system defined in claim 70 wherein the proximal balloon drives the prongs of the proximal pronged attachment ring through the graft and into the patient's tissue at the distal attachment site when the proximal balloon is further inflated during at least part of graft delivery.

72. The system defined in claim 71 wherein the distal balloon is configured to drive the prongs of the distal pronged attachment ring through the graft and into the patient's tissue at the distal attachment site when the distal balloon is further inflated during at least part of graft delivery.

* * * * *